(12) United States Patent
    Ostergard

(10) Patent No.: US 10,660,781 B1
(45) Date of Patent: May 26, 2020

(54) ANKLE BRACE

(71) Applicant: Doak Ostergard, Lincoln, NE (US)

(72) Inventor: Doak Ostergard, Lincoln, NE (US)

(*) Notice: Subject to any disclaimer, the term of this patent is extended or adjusted under 35 U.S.C. 154(b) by 460 days.

(21) Appl. No.: 15/593,975

(22) Filed: May 12, 2017

Related U.S. Application Data

(60) Division of application No. 13/871,094, filed on Apr. 26, 2013, now abandoned, which is a continuation-in-part of application No. 13/134,087, filed on May 27, 2011, now Pat. No. 8,657,773.

(51) Int. Cl.
*A61F 5/01* (2006.01)
*A43B 5/00* (2006.01)
*A43C 1/00* (2006.01)
*A43C 15/16* (2006.01)
*A43C 5/00* (2006.01)

(52) U.S. Cl.
CPC .............. *A61F 5/0111* (2013.01); *A43B 5/00* (2013.01); *A43C 1/00* (2013.01); *A43C 5/00* (2013.01); *A43C 15/16* (2013.01)

(58) Field of Classification Search
CPC .... A43B 5/02; A43B 7/20; A43B 5/18; A43B 5/163; A61F 5/0111; A61F 13/066; A61F 13/06; A61F 5/0127; A43C 5/00; A43C 11/008
USPC ......... 602/23, 27, 5, 28; 36/88, 89, 11.5, 91, 36/92, 140; 128/882
See application file for complete search history.

(56) References Cited

U.S. PATENT DOCUMENTS

| | | |
|---|---|---|
| 2008/0082034 A1 | 4/2008 | Wilkerson |
| 2008/0306422 A1 | 12/2008 | McChesney et al. |
| 2009/0216167 A1 | 8/2009 | Harris |
| 2009/0247923 A1 | 10/2009 | Lundberg |
| 2012/0302933 A1 | 11/2012 | Ostergard |
| 2017/0071774 A1* | 3/2017 | Ostergard ............... A43C 1/00 |

* cited by examiner

*Primary Examiner* — Anna K Kinsaul
*Assistant Examiner* — Caitlin A Carreiro
(74) *Attorney, Agent, or Firm* — Dennis L. Thomte; Thomte Patent Law Office LLC

(57) ABSTRACT

An ankle brace which is positioned on an ankle of a person which incorporates a tensioning structure which permits full range of motion to the ankle joint but which prevents the ankle joint from moving past its normal range of motion to protect the ankle joint.

15 Claims, 6 Drawing Sheets

ANKLE BRACE

CROSS REFERENCE TO RELATED APPLICATION

This is a Divisional application of application Ser. No. 13/871,094, filed on Apr. 26, 2013 entitled ANKLE BRACE, which is a Continuation-In-Part of application Ser. No. 13/134,087, filed on May 27, 2011, entitled ANKLE BRACE.

BACKGROUND OF THE INVENTION

Field of the Invention

This invention relates to an ankle brace and more particularly to an ankle brace including a tensioning system which functionally stabilizes the ankle as it reaches extreme ranges of motion.

Description of the Related Art

Conventional braces for protecting joints of the body do so by restricting or limiting motion of the joint to which it is applied to prevent a new injury or to protect a pre-existing injury. An ankle joint, just like all the joints in the human body, has a natural range of motion that it can move through without causing damage to itself. As it reaches the end of these ranges, the body has structure such as ligaments and tendons to create tension to end range of motion and protect the joint. Many of the prior art ankle braces do prevent the ankle from exceeding its extreme ranges of motion but do not provide the necessary flexibility to permit the athlete to function normally.

Applicant's ankle brace described and shown in the co-pending application represents an improvement in the ankle brace art. The instant invention represents a further improvement in the ankle brace art.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

An ankle brace is disclosed for use with a cleated athletic shoe having a sole with a lower surface, with cleats extending downwardly therefrom, a lateral side and a medial side, an upper part with an upper end, a lacing closure, with upper and lower ends, including a plurality of spaced-apart pairs of eyelets adapted to have a shoe lace threaded therein. The brace of this invention includes a flexible lateral portion having an upper end, a lower end, a forward end, a rearward end, an outer side and an inner side. The upper end of the lateral portion has a plurality of spaced-apart first eyelets formed therein at the forward end thereof. A first loop is secured to the outer side of the lateral portion adjacent the eyelets at the forward end thereof. A second loop is secured to the outer side of the lateral portion rearwardly of the first loop. A third loop is secured to the outer side of the lateral portion below the eyelets at the forward end of the lateral portion and below the first loop thereof. The lateral portion also has an eyelet formed therein rearwardly of the first eyelets. A patch or strip of hook fasteners secured to the outer surface of the lateral portion at the rearward end thereof. The lateral portion is removably positioned adjacent the lateral side of the upper part of the shoe with the lower end of the lateral portion extending beneath the sole of the shoe.

The ankle brace also includes a flexible medial portion having an upper end, a lower end, a forward end, a rearward end, an outer side and an inner side. The upper end of the medial portion has a plurality of spaced-apart first eyelets formed therein at the forward end thereof. A first loop is secured to the outer side of the medial portion adjacent the eyelets at the forward end thereof. A second loop is secured to the outer side of the medial portion rearwardly of the first loop. A third loop is secured to the outer side of the medial portion below the eyelets at the forward end of the medial portion and below the first loop thereof. The medial portion has an eyelet formed therein rearwardly of the first eyelets thereof.

The lower end of the medial portion extends beneath the sole of the shoe with the lower ends of the lateral and medial portions being joined together beneath the sole of the shoe. The rearward ends of the lateral and medial portions are spaced apart.

An elongated first strap having first and second ends and inner and outer surfaces is also provided. The first end of the first strap is secured to the medial portion at the rearward end thereof. The inner surface of the first strap has loop fasteners thereon. The rearward ends of the lateral and medial portions are spaced apart. The first strap is selectively adjustably secured to the patch of hook fasteners at the outer rearward side of the medial portion.

The ankle brace of this invention also includes a flexible and stretchable body member having upper and lower ends, a lateral side portion, a medial side portion, and a heel portion. The lower end of the lateral side portion of the body member is secured to the lateral portion. The lower end of the medial side portion of the body member is secured to the medial portion. The heel portion of the body member is secured to the spaced-apart rearward ends of the lateral and medial portions and extends therebetween. A second flexible and stretchable strap is provided having a first end, a second end, an upper end, a lower end, and inner and outer sides. The lower end of the second strap is secured to the upper end of the body member so that the first and second ends of the second strap extend forwardly from the body member. The outer side of the second strap has loop fasteners thereon at the first end thereof. The brace also includes a third flexible strap having a first end, a second end, an outer side and an inner side. The first end of the third strap is secured to the second end of the second strap. The inner side of the third strap has hook fasteners thereon for adjustable attachment to the loop fasteners on the second strap at the first end of the second strap. A fourth flexible non-stretchable strap is provided having first and second ends with the fourth strap being secured to the outer side of the second strap. The first end of the fourth strap has a pair of eyelets formed therein. The second end of the fourth strap has a pair of eyelets formed therein. A loop is secured to the fourth strap at the first end thereof and a loop is secured to the fourth strap at the second end thereof. A lace member adjustably extends through the eyelets on the first and second ends of the fourth strap.

The ankle brace of this invention includes a flexible and stretchable lateral tensioning cord having first and second ends. The first end of the lateral tensioning cord is secured to the fourth strap at the first end thereof. The lateral tensioning cord extends from its fixed first end downwardly and forwardly through the second loop on the lateral portion, thence forwardly through the first loop on the lateral portion, thence downwardly and rearwardly through the third loop on the lateral portion, thence upwardly and rearwardly through the second loop on the lateral portion, thence rearwardly through the loop at the first end of the fourth strap, thence downwardly therefrom. The second end of the lateral tensioning cord is secured to the lateral portion. A flexible and stretchable medial tensioning cord is also provided having first and second ends with the first end of the medial tensioning cord being secured to the fourth strap at the second end thereof. The medial tensioning cord extends from its fixed first end downwardly and forwardly through the second loop on the medial portion, thence forwardly through the first loop on the medial portion, thence downwardly and rearwardly through the third loop on the medial portion, thence upwardly and rearwardly through the second loop on the medial portion, thence rearwardly through the loop at the second end of the fourth strap, thence downwardly therefrom. The second end of the medial tensioning cord is secured to the medial portion.

The ankle brace also includes fifth and sixth straps having first and second ends. The first end of the fifth strap is secured to the lateral portion with the second end of the fifth strap being adjustably secured to the medial portion 92. The sixth strap has its first end secured to the medial portion 92 and has its second end selectively adjustably secured to the lateral portion 36. The ankle brace of this invention permits the wearers ankle to move through its normal range of motion and yieldably prevents the ankle from moving beyond its normal range motion thereby protecting the ankle.

It is therefore a principal object of the invention to provide an improved ankle brace.

A further object of the invention is to provide an ankle brace for use with a cleated athletic shoe which permits the wearer's ankle to move through its normal range of motion but which yieldably prevents the ankle from moving beyond its normal range of motion thereby protecting the ankle.

A further object of the invention is to provide an ankle brace of the type described which does not interfere with the normal movement of the person's ankle.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
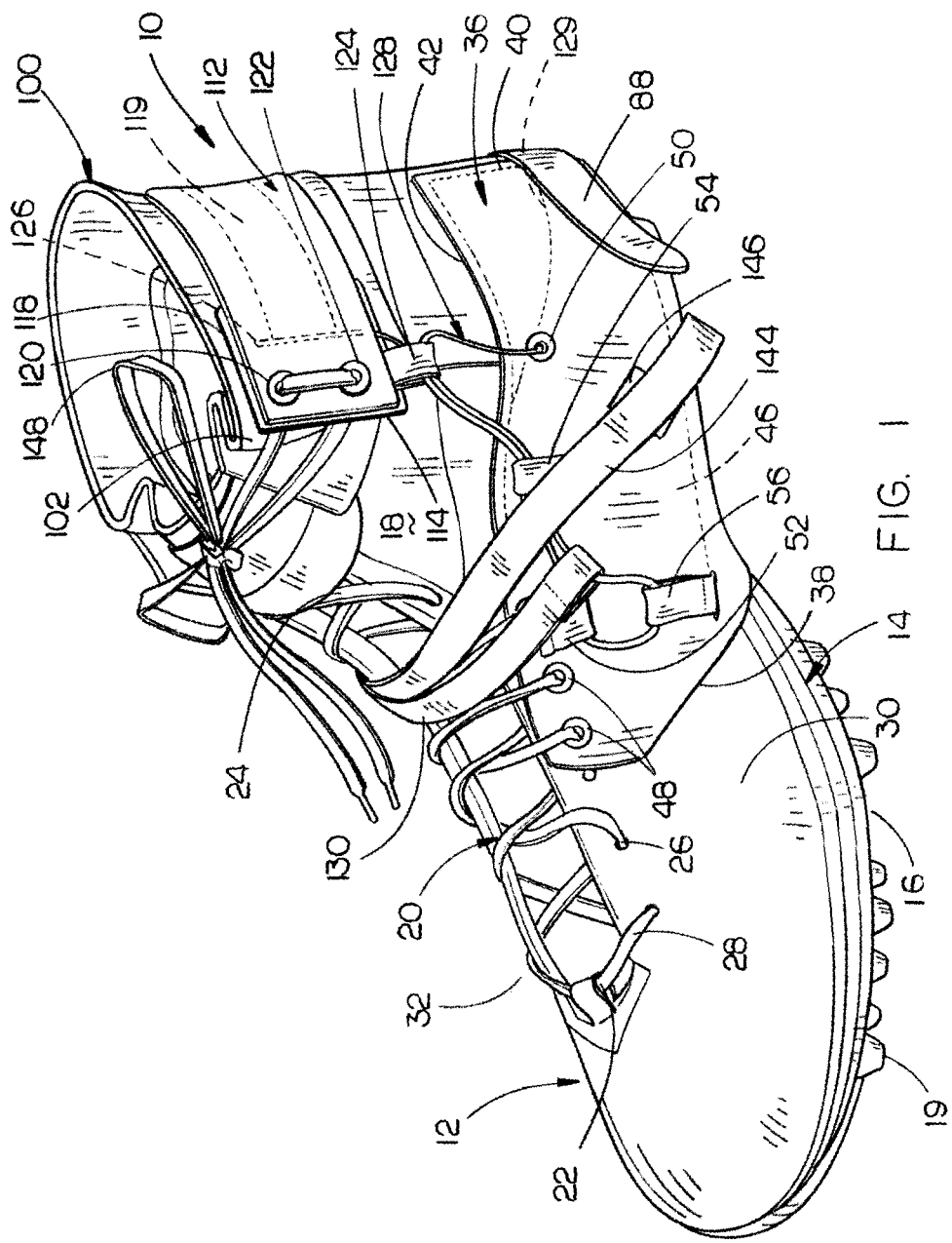
FIG. 1 is a perspective view of the ankle brace of this invention mounted on an athletic shoe.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The ankle brace of this invention is referred to generally by the reference numeral 10. Ankle brace 10 is designed to be attached to an athletic shoe 12 having a sole 14 with an underside 16, and an upper part 18. A plurality of cleats 19 extend downwardly from the underside 16 of sole 14. Upper part 18 has a lacing closure structure 20 having a lower end 22 and an upper end 24. Lacing closure has a plurality of eyelets, grommets or lace openings 26 designed to receive a shoelace 28 in conventional fashion. Shoe 12 will be described as having a lateral side 30, a medial side 32 and a heel counter 34.

Ankle brace 10 includes a lateral portion 36 having a forward end 38, a rearward end 40, an upper end 42 and a lower end 44. Lower end 44 of lateral portion 36 extends partially below sole 14 as will be described in more detail hereinafter. Lateral portion 36 is comprised of a flexible, non-stretchable material such as polyester. The inner side of lateral portion 36 has a flexible, non-stretchable reinforcing or stiffening member 46 secured to the upper portion thereof by stitching or the like. Member 46 is preferably comprised of a plastic material. The upper forward end of lateral portion 36 has a plurality of spaced-apart grommets or eyelets 48 formed therein. Preferably, four eyelets 48 are formed in lateral portion 36. A grommet 50 is formed in lateral portion 36 rearwardly of the rearward-most grommet 48. A loop 52 is secured to the outer surface of lateral portion 36 between a pair of grommets 48. A loop 54 is secured to the outer surface of lateral portion 30 adjacent the rearward-most grommet 48. A loop 56 is secured to the outer surface of lateral portion 36 below loop 52. The lower rearward end 44 of lateral portion 36 has a notch 58 formed therein. A notch 60 is also formed in the lower end 44 of lateral portion 36 forwardly of notch 58.

Ankle brace 10 also includes a medial portion 62 having a forward end 64, a rearward end 66, an upper end 68 and a lower end 70. Medial portion 62 is comprised of a flexible, non-stretchable material such as polyester. Lower end 70 of medial portion 62 extends partially below sole 14 and is secured to lower end 44 of lateral portion 36. The inner side of medial portion 62 has a flexible, non-stretchable reinforcing or stiffening member 72 secured to the upper portion thereof by stitching or the like. Member 72 is preferably comprised of a plastic material. The upper forward end of medial portion 62 has a plurality of spaced-apart grommets or eyelets 74 formed therein, the number of which is equal to the number of grommets or eyelets 48 formed in lateral portion 36. A grommet 76 is formed in medial portion 62 rearwardly of the rearward-most grommet 74. A loop 78 is secured to the outer surface of medial portion 62 between a pair of the grommets 74. A loop 80 is secured to the outer surface of medial portion 62 adjacent the rearward-most grommet 74. A loop 82 is secured to the outer surface of medial portion 62 below loop 78.

The lower end 70 of medial portion 62 has a notch 84 formed therein which registers with notch 58 in lateral portion 36. The lower end 70 of medial portion 62 also has a notch 86 formed therein which registers with notch 60 of lateral portion 36. The lower ends 44 and 70 of medial portion 62 and lateral portion 36 respectively are secured together by stitching 87 or the like.

As seen in the drawings, the rearward ends of lateral portion 36 and medial portion 62 are spaced-apart. The rearward end of medial portion 62 has a first strap 88 secured thereto which extends therefrom. The inner surface of strap 88 has loop fasteners thereon. The rearward end of lateral portion 36 has a patch 90 of hook fasteners to enable the strap 88 to be adjustably secured thereto.

The numeral 92 refers to a flexible and stretchable body member preferably comprised of neoprene or the like which is secured to lateral portion 36 and medial portion 62 as will now be described. Body member 92 includes a lateral side portion 94, a medial side portion 96 and a heel portion 98. The lower end of lateral side portion 94 of body member 92 is secured to the upper end of lateral portion 36 by stitching or the like. The lower end of medial side portion 96 is secured to the upper end of medial portion 62 by stitching or the like. Heel portion 98 is positioned between the rearward ends of lateral portion 36 and medial portion 62 and is secured thereto by stitching or the like.

The numeral 100 refers to an elongated second strap having ends 102 and 104, an upper end 106 and a lower end 108. The lower end 108 of strap 100 is secured to the upper end of flexible and stretchable body member 92 so that the ends 102 and 104 extend forwardly from the forward ends of flexible and stretchable body member 92. The outer surface of strap 100 has loop fastener material thereon.

A short third strap 110 has one end secured to end 102 of strap 100 and extends therefrom. The inner side of strap 110 has hook fasteners thereon for adjustable connection to the loop fasteners on the outer side of end 104 of strap 100.

A flexible and non-stretchable fourth strap 112, having ends 114 and 116, is secured to strap 100 at the outer side thereof by stitching or the like. A plastic reinforcing member 118 is secured to the inner side of strap 112 at end 114. An elongated, flexible reinforcing or stiffening member 119 is positioned at the inner side of strap 112. Grommets 120 and 122 are formed in the end 114 of strap 112 and reinforcing member 118. At least one loop 124 is secured to and extends downwardly from end 114 of strap 112 and reinforcing member 118.

End 126 of lateral tensioning cord 128 is secured to strap 112 and reinforcing member 118 adjacent end 114 of strap 112. Tensioning cord 128 extends downwardly and forwardly from strap 112 and reinforcing member 118, through loop 54, thence through loop 52, thence downwardly therefrom, thence rearwardly through loop 56, thence upwardly and rearwardly through loop 54, thence upwardly and rearwardly through loop 124, and thence downwardly and rearwardly through grommet 50 for attachment to reinforcing member 46 at 129.

One end of an elongated fifth strap 130 is slidably mounted on cord 128 between loops 54 and 56. The inner surface of strap 130 is provided with loop fasteners thereon for adjustable attachment to a patch or strap of hook fasteners 131 secured to the outer side of medial portion 62. A plastic reinforcing member 132 is secured to the inner side of strap 112 at end 116. Grommets 134 and 136 are formed in end 116 of strap 112 and reinforcing member 132. At least one loop 138 is secured to and extends downwardly from end 116 and reinforcing member 132.

End 140 of tensioning cord 142 is secured to strap 112 and reinforcing member 132 adjacent end 116 of strap 112. Tensioning cord 142 extends downwardly and forwardly from strap 112 and reinforcing member 132, through loop 80, thence through loop 78, thence downwardly therefrom, thence rearwardly through loop 82, thence upwardly and rearwardly through loop 80, thence upwardly and rearwardly through loop 138, and thence downwardly and rearwardly through grommet 76 for attachment to reinforcing member 72.

One end of an elongated sixth strap 144 is slidably mounted on cord 142 between loops 78 and 80. The inner surface of strap 144 is provided with loop fasteners thereon for adjustable attachment to a patch or strap of hook fasteners 146 secured to the outer side of lateral portion 36.

Figure 2:
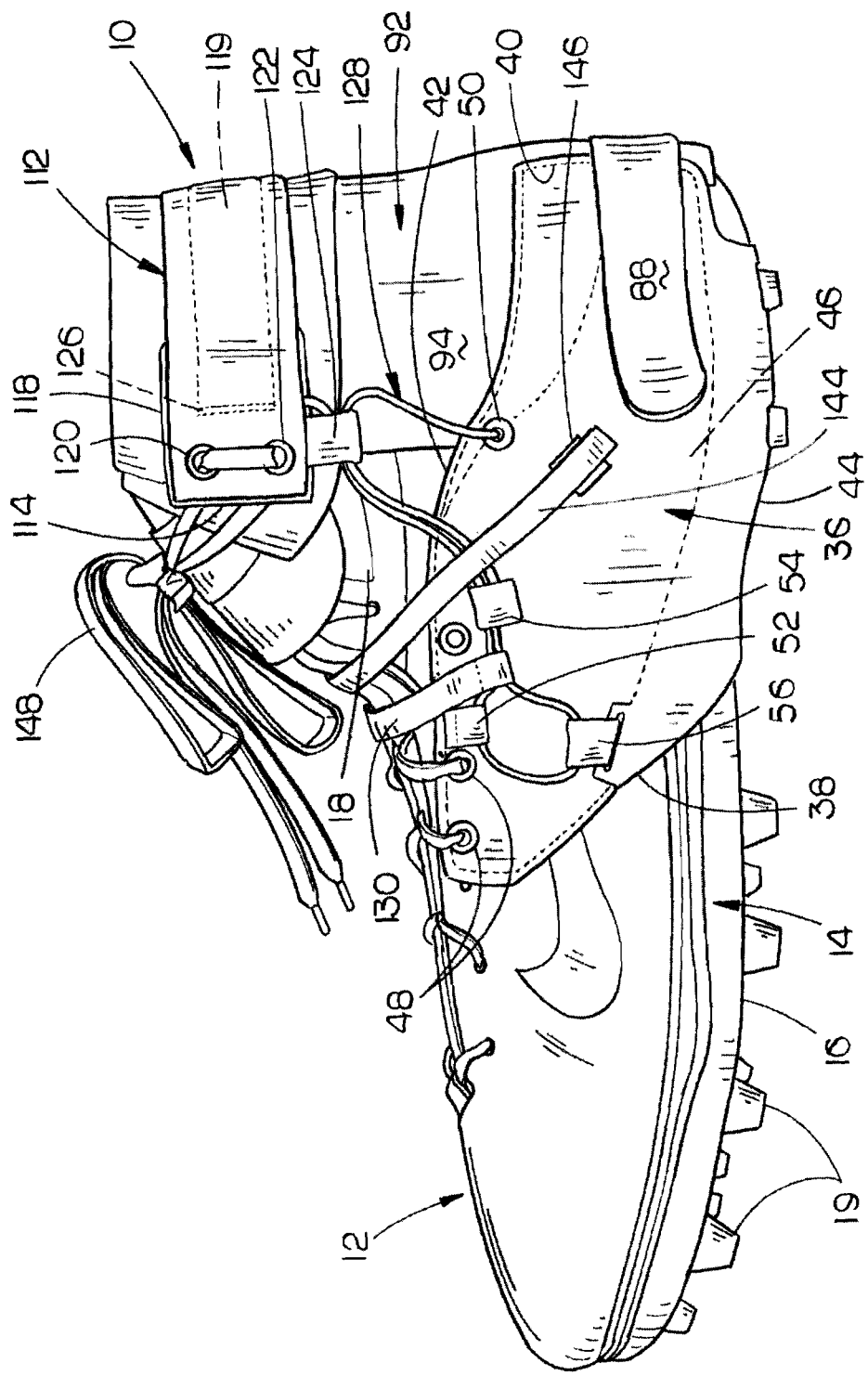
FIG. 2 is a side view of the ankle brace of FIG. 1.
Figure 3:
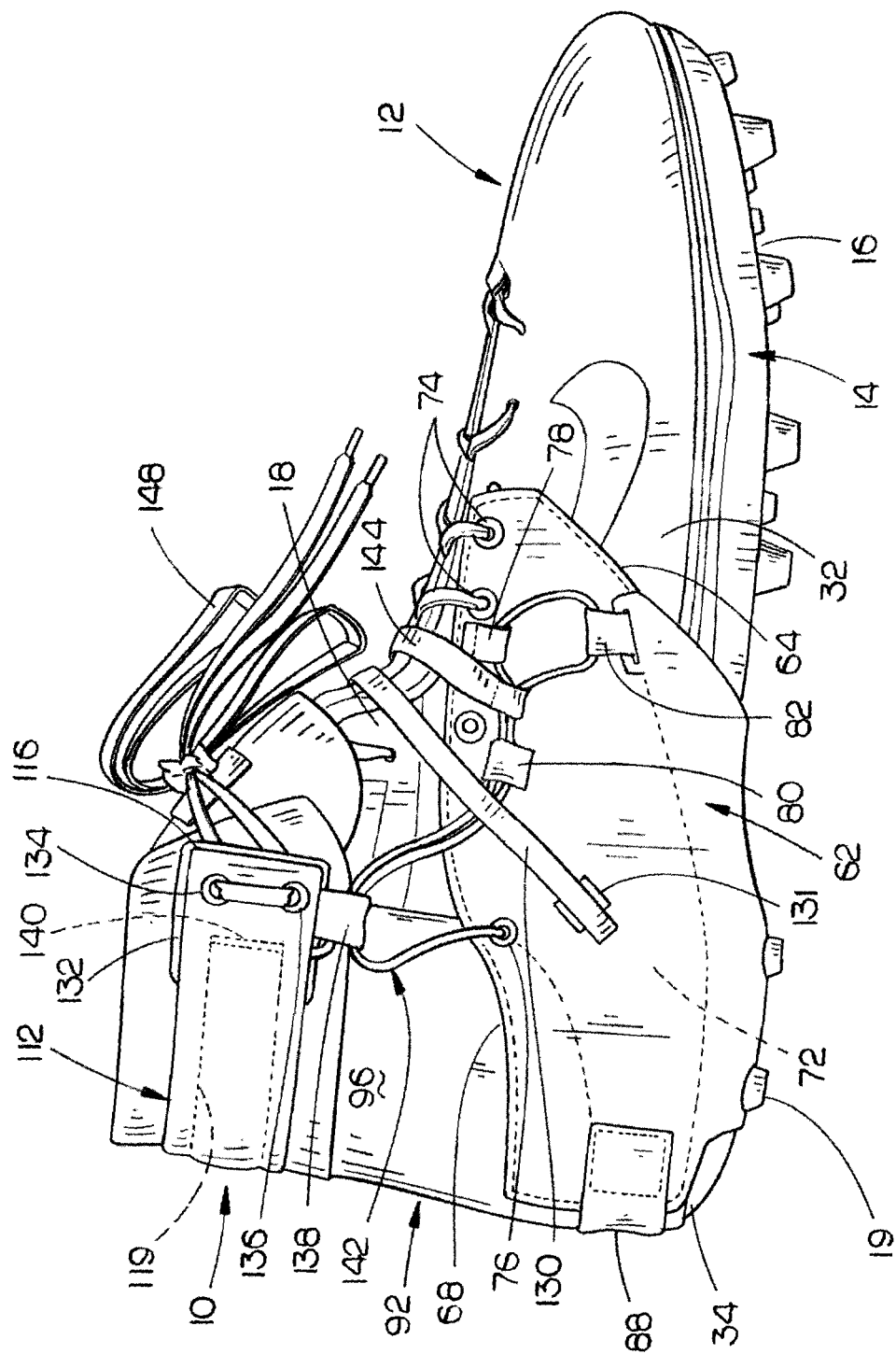
FIG. 3 is a side view of the ankle brace as seen from the medial side thereof.
Figure 4:
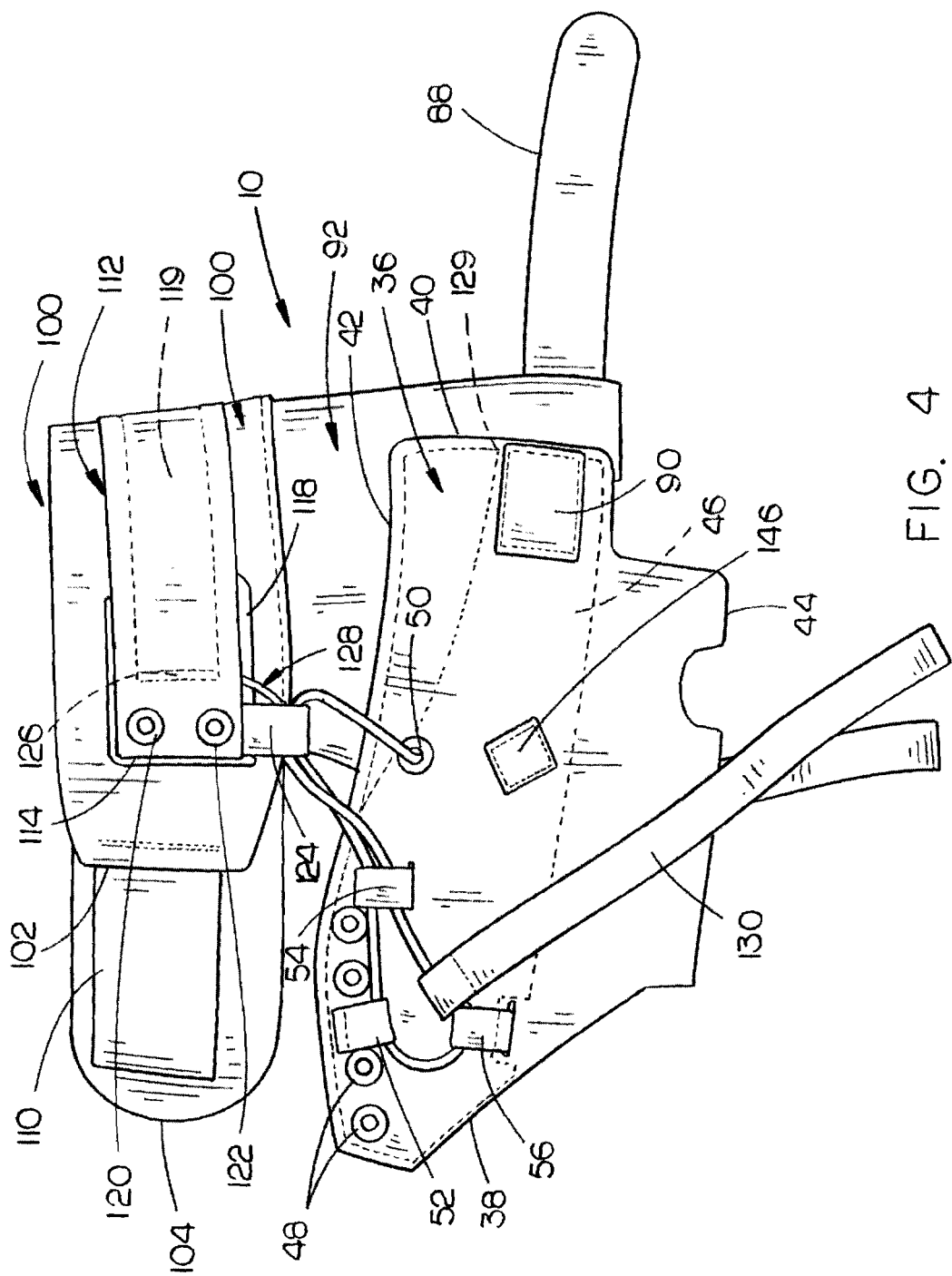
FIG. 4 is a side view of the ankle brace as seen from the lateral side thereof.
Figure 5:
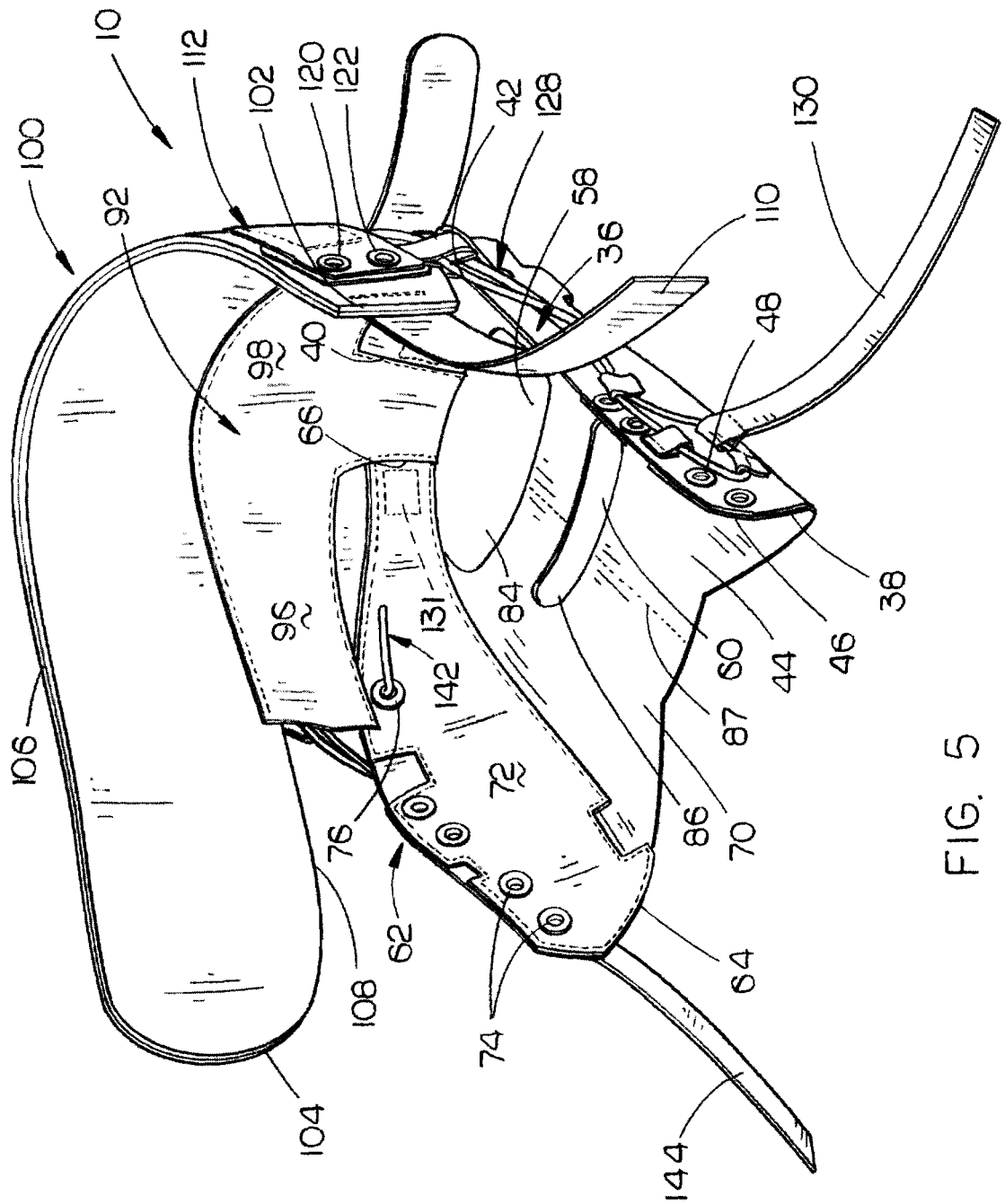
FIG. 5 is a perspective view of the ankle brace of this invention.

In use, the brace 10 is positioned on the shoe 12 as generally seen in FIGS. 1-3 but the lace member 148 is not tied, the strap 88 is not secured to patch or strip 90 and the straps 130 and 144 are not secured to strips or patches 131 and 146 respectively. The shoe lace 28 is threaded through some of the lower lace openings or eyelets 26 and through at least some of the eyelets 48 of lateral portion 36 and through some of the eyelets 74 of medial portion 62. The shoe lace 28 will then be threaded through the remaining eyelets 26 and tied at the upper end of the shoe 12.

Figure 6:
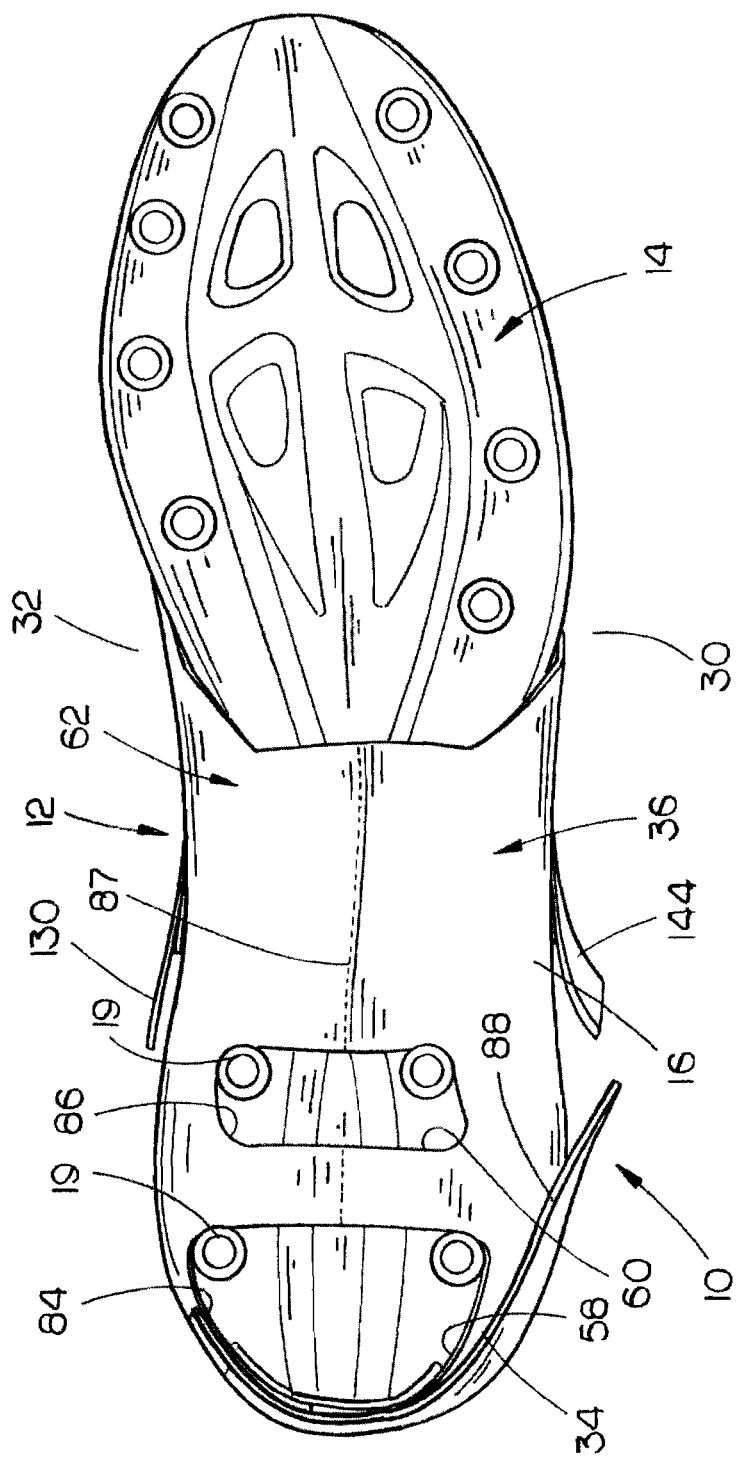
FIG. 6 is a bottom view of the athletic shoe having the ankle brace of this invention mounted thereon.

The lace member 148 is threaded through the eyelets 120, 122 on end 114 of strap 112 and through eyelets 134 and 136 at end 116 of strap 112. The lace member 148 is then tightened and tied. The strap 88 is then secured to patch 90. Straps 130 and 144 are then adjustably tightened and secured as described hereinabove. As seen in FIG. 6, some of the cleats 19 extend downwardly through the registering notches 58 and 84 and some of the cleats 19 extend downwardly through the registering notches 60 and 86.

The ankle brace 10 permits the ankle of the person to move through its natural range of motion either laterally, medially, fore and aft. When the ankle moves towards the end of its normal range of motion, the tensioning cords 128 and 142 resist further motion to protect the ankle. Ankle support is also provided by the lateral and medial portions 36 and 62 and the reinforcing members associated therewith. Ankle support is also provided by the flexible and stretchable member 92 which enables the person's ankle to move through its normal range of motion.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. An ankle brace for use with an athletic shoe having a lateral side, a medial side, an upper part with an upper end, a sole with a lower cleated surface, a lacing closure, with upper and lower ends, including a plurality of spaced-apart pairs of eyelets adapted to have a shoe lace threaded therein, comprising:

a flexible lateral portion having an upper end, a lower end, a forward end, a rearward end, an outer side and an inner side;

said upper end of said flexible lateral portion having a plurality of spaced-apart first eyelets formed therein at said forward end thereof;

a first loop secured to said outer side of said flexible lateral portion adjacent said plurality of spaced-apart first eyelets at said forward end thereof;

a second loop secured to said outer side of said flexible lateral portion rearwardly of said first loop;

a third loop secured to said outer side of said flexible lateral portion below said plurality of spaced-apart first eyelets at said forward end of said flexible lateral portion and below said first loop;

said flexible lateral portion having a strip of hook fasteners secured to the outer side thereof at said rearward end thereof;

said flexible lateral portion being removably positioned adjacent the lateral side of the athletic shoe;

said lower end of said flexible lateral portion extending beneath the sole of the athletic shoe;

a flexible medial portion having an upper end, a lower end, a forward end, a rearward end, an outer side and an inner side;

said upper end of said flexible medial portion having a plurality of spaced-apart first eyelets formed therein at said forward end thereof;

a first loop secured to said outer side of said flexible medial portion adjacent said plurality of spaced-apart first eyelets at said forward end thereof;

a second loop secured to said outer side of said flexible medial portion rearwardly of said first loop thereof;

a third loop secured to said outer side of said flexible medial portion below said plurality of spaced-apart first eyelets at said forward end of said flexible medial portion and below said first loop thereof;

an elongated first strap having first and second ends and inner and outer surfaces;

said first end of said elongated first strap being secured to said flexible medial portion at said rearward end thereof;

said inner surface of said elongated first strap having loop fasteners thereon;

said elongated first strap being selectively adjustably secured to said strip of hook fasteners secured to the outer side of said flexible lateral portion;

said lower end of said flexible medial portion extending beneath the sole of the athletic shoe;

said lower ends of said flexible lateral and medial portions being joined together beneath the sole of the athletic shoe;

said rearward ends of said flexible lateral and medial portions being spaced-apart;

a flexible and stretchable body member having upper and lower ends, a lateral side portion, a medial side portion, and a heel portion;

said lower end of said lateral side portion of said flexible and stretchable body member being secured to said flexible lateral portion;

said lower end of said medial side portion of said flexible and stretchable body member being secured to said flexible medial portion;

said heel portion of said flexible and stretchable body member being secured to said rearward ends of said flexible lateral and medial portions and extending therebetween;

a second flexible and stretchable strap having a first end, a second end, an upper end, a lower end, and inner and outer sides;

said lower end of said second flexible and stretchable strap being secured to said upper end of said flexible and stretchable body member so that said first and second ends of said second flexible and stretchable strap extend forwardly from said flexible and stretchable body member;

said outer side of said second flexible and stretchable strap having loop fasteners thereon at said second end thereof;

a third strap having a first end, a second end, an outer side and an inner side;

said first end of said third strap being secured to said first end of said second flexible and stretchable strap;

said inner side of said third strap having hook fasteners thereon for adjustable attachment to said loop fasteners on said second flexible and stretchable strap at said second end of said second flexible and stretchable strap;

a fourth non-stretchable strap having first and second ends;

said fourth non-stretchable strap being secured to said outer side of said second flexible and stretchable strap;

said first end of said fourth non-stretchable strap having at least one eyelet formed therein;

said second end of said fourth non-stretchable strap having at least one eyelet formed therein;

a loop secured to said fourth non-stretchable strap at said first end thereof;

a loop secured to said fourth non-stretchable strap at said second end thereof;

a first lace member adjustably extending through said at least one eyelet on said first and second ends of said fourth non-stretchable strap;

a flexible and stretchable lateral tensioning cord having first and second ends;

said first end of said flexible and stretchable lateral tensioning cord being secured to said fourth non-stretchable strap at said first end thereof;

said flexible and stretchable lateral tensioning cord extending from said first end thereof downwardly and forwardly through said second loop on said flexible lateral portion, thence forwardly through said first loop on said flexible lateral portion, thence downwardly and rearwardly through said third loop on said flexible lateral portion, thence upwardly and rearwardly through said second loop on said flexible lateral portion, thence rearwardly through said loop at said first end of said fourth non-stretchable strap, thence downwardly therefrom;

said second end of said flexible and stretchable lateral tensioning cord being secured to said flexible lateral portion;

a flexible and stretchable medial tensioning cord having first and second ends;

said first end of said flexible and stretchable medial tensioning cord being secured to said fourth non-stretchable strap at said second end thereof;

said flexible and stretchable medial tensioning cord extending from its said first end downwardly and forwardly through said second loop on said flexible medial portion, thence forwardly through said first loop on said flexible medial portion, thence downwardly and rearwardly through said third loop on said flexible medial portion, thence upwardly and rearwardly through said second loop on said flexible medial portion, thence rearwardly through said loop at said second end of said fourth non-stretchable strap, thence through said eyelet which is positioned rearwardly of said plurality of spaced-apart first eyelets on said flexible medial portion;

said second end of said flexible and stretchable medial tensioning cord being secured to said flexible medial portion;

the shoe lace of the athletic shoe also being threaded through some of said plurality of spaced-apart first eyelets formed in said flexible lateral portion and through some of said plurality of spaced-apart first eyelets in said flexible medial portion.

2. The ankle brace of claim 1 further including elongated fifth and sixth straps having first and second ends; said first end of said elongated fifth strap being secured to said flexible and stretchable lateral tensioning cord; said second end of said elongated fifth strap being selectively adjustably secured to the outer side of said flexible medial portion; said first end of said elongated sixth strap being secured to said flexible and stretchable medial tensioning cord; said second end of said elongated sixth strap being selectively adjustably secured to said outer side of said flexible lateral portion.

3. The ankle brace of claim 2 wherein said first end of said elongated fifth strap is secured to said flexible and stretchable lateral tensioning cord between said first and third loops of said flexible lateral portion and wherein said first end of said elongated sixth strap is secured to said flexible and stretchable medial tensioning cord between said first and second loops of said flexible medial portion.

4. The ankle brace of claim 3 wherein said first end of said elongated fifth strap is slidably secured to said flexible and stretchable lateral tensioning cord and wherein said first end of said elongated sixth strap is slidably secured to said flexible and stretchable medial tensioning cord.

5. The ankle brace of claim 1 wherein said flexible lateral portion has an eyelet formed thereon rearwardly of said plurality of spaced-apart first eyelets thereof and wherein said flexible medial portion has an eyelet formed therein rearwardly of said plurality of spaced-apart first eyelets thereof; said second end of said flexible and stretchable lateral tensioning cord extending through said eyelet which is positioned rearwardly of said plurality of spaced-apart first eyelets of said flexible lateral portion for connection to said flexible lateral portion; said second end of said flexible and stretchable medial tensioning cord extending through said eyelet which is positioned rearwardly of said plurality of spaced-apart first eyelets of said flexible medial portion for connection to said flexible medial portion.

6. The ankle brace of claim 1 wherein a reinforcing member is positioned at the inner side of said flexible lateral portion and is secured thereto and wherein a reinforcing member is positioned at the inner side of said flexible medial portion and is secured thereto.

7. The ankle brace of claim 1 wherein a reinforcing member is positioned between said fourth non-stretchable strap and said third strap.

8. The ankle brace of claim 1 wherein said lower ends of said flexible lateral and medial portions have openings formed therein which receive some of the lower cleated surface of the sole extending downwardly therethrough.

9. An ankle brace for use with an athletic shoe having a lateral side and a medial side, an upper part with an upper end, a sole a lacing closure, with upper and lower ends, including a plurality of spaced-apart pairs of eyelets adapted to have a shoe lace threaded therein, comprising:
a flexible lateral portion having an upper end, a lower end, a forward end, a rearward end, an outer side and an inner side;
said upper end of said flexible lateral portion having a plurality of spaced-apart first eyelets formed therein at said forward end thereof;
a first loop secured to said outer side of said flexible lateral portion adjacent said plurality of spaced-apart first eyelets at said forward end thereof;
a second loop secured to said outer side of said flexible lateral portion rearwardly of said first loop;
a third loop secured to said outer side of said flexible lateral portion below said plurality of spaced-apart first eyelets at said forward end of said flexible lateral portion and below said first loop;
said flexible lateral portion having a strip of hook fasteners secured to the outer side thereof at said rearward end thereof;
said flexible lateral portion being removably positioned adjacent the lateral side of of the athletic shoe;
said lower end of said flexible lateral portion extending beneath the sole of the athletic shoe;
a flexible medial portion having an upper end, a lower end, a forward end, a rearward end, an outer side and an inner side;
said upper end of said flexible medial portion having a plurality of spaced-apart first eyelets formed therein at said forward end thereof;
a first loop secured to said outer side of said flexible medial portion adjacent said plurality of spaced-apart first eyelets at said forward end thereof;
a second loop secured to said outer side of said flexible medial portion rearwardly of said first loop thereof;
a third loop secured to said outer side of said flexible medial portion below said plurality of spaced-apart first eyelets at said forward end of said flexible medial portion and below said first loop thereof;
an elongated first strap having first and second ends and inner and outer surfaces;
said first end of said elongated first strap being secured to said flexible medial portion at said rearward end thereof;
said inner surface of said elongated first strap having loop fasteners thereon;
said elongated first strap being selectively adjustably secured to said strip of hook fasteners secured to the outer side of said flexible lateral portion;
said lower end of said flexible medial portion extending beneath the sole of the athletic shoe;
said lower ends of said flexible lateral and medial portions being joined together beneath the sole of the athletic shoe;
said rearward ends of said flexible lateral and medial portions being spaced-apart;
a flexible and stretchable body member having upper and lower ends, a lateral side portion, a medial side portion, and a heel portion;
said lower end of said lateral side portion of said flexible and stretchable body member being secured to said flexible lateral portion;
said lower end of said medial side portion of said flexible and stretchable body member being secured to said flexible medial portion;
said heel portion of said flexible and stretchable body member being secured to said rearward ends of said flexible lateral and medial portions and extending therebetween;
a second flexible and stretchable strap having a first end, a second end, an upper end, a lower end, and inner and outer sides;
said lower end of said second flexible and stretchable strap being secured to said upper end of said flexible and stretchable body member so that said first and second ends of said second flexible and stretchable strap extend forwardly from said flexible and stretchable body member;

said outer side of said second flexible and stretchable strap having loop fasteners thereon at said second end thereof;

a third strap having a first end, a second end, an outer side and an inner side;

said first end of said third strap being secured to said first end of said second flexible and stretchable strap;

said inner side of said third strap having hook fasteners thereon for adjustable attachment to said loop fasteners on said second flexible and stretchable strap at said second end of said second flexible and stretchable strap;

a fourth non-stretchable strap having first and second ends;

said fourth non-stretchable strap being secured to said outer side of said second flexible and stretchable strap;

said first end of said fourth non-stretchable strap having at least one eyelet formed therein;

said second end of said fourth non-stretchable strap having at least one eyelet formed therein;

a loop secured to said fourth non-stretchable strap at said first end thereof;

a loop secured to said fourth non-stretchable strap at said second end thereof;

a first lace member adjustably extending through said at least one eyelet on said first and second ends of said fourth non-stretchable strap;

a flexible and stretchable lateral tensioning cord having first and second ends;

said first end of said flexible and stretchable lateral tensioning cord being secured to said fourth non-stretchable strap at said first end thereof;

said flexible and stretchable lateral tensioning cord extending from its said first end downwardly and forwardly through said second loop on said flexible lateral portion, thence forwardly through said first loop on said flexible lateral portion, thence downwardly and rearwardly through said third loop on said flexible lateral portion, thence upwardly and rearwardly through said second loop on said flexible lateral portion, thence rearwardly through said loop at said first end of said fourth non-stretchable strap, thence downwardly therefrom;

said second end of said flexible and stretchable lateral tensioning cord being secured to said flexible lateral portion;

a flexible and stretchable medial tensioning cord having first and second ends;

said first end of said flexible and stretchable medial tensioning cord being secured to said fourth non-stretchable strap at said second end thereof;

said flexible and stretchable medial tensioning cord extending from its said first end downwardly and forwardly through said second loop on said flexible medial portion, thence forwardly through said first loop on said flexible medial portion, thence downwardly and rearwardly through said third loop on said flexible medial portion, thence upwardly and rearwardly through said second loop on said flexible medial portion, thence rearwardly through said loop at said second end of said fourth non-stretchable strap, thence through said eyelet which is positioned rearwardly of said plurality of spaced-apart first eyelets on said flexible medial portion;

said second end of said flexible and stretchable medial tensioning cord being secured to said flexible medial portion;

the shoe lace of the athletic shoe also being threaded through some of said plurality of spaced-apart first eyelets formed in said flexible lateral portion and through some of said plurality of spaced-apart first eyelets in said flexible medial portion.

10. The ankle brace of claim 9 further including elongated fifth and sixth straps having first and second ends; said first end of said elongated fifth strap being secured to said flexible and stretchable lateral tensioning cord; said second end of said elongated fifth strap being selectively adjustably secured to the outer side of said flexible medial portion; said first end of said elongated sixth strap being secured to said flexible and stretchable medial tensioning cord; said second end of said elongated sixth strap being selectively adjustably secured to said outer side of said flexible lateral portion.

11. The ankle brace of claim 10 wherein said first end of said elongated fifth strap is secured to said flexible and stretchable lateral tensioning cord between said first and third loops of said flexible lateral portion and wherein said first end of said elongated sixth strap is secured to said flexible and stretchable medial tensioning cord between said first and second loops of said flexible medial portion.

12. The ankle brace of claim 11 wherein said first end of said elongated fifth strap is slidably secured to said flexible and stretchable lateral tensioning cord and wherein said first end of said elongated sixth strap is slidably secured to said flexible and stretchable medial tensioning cord.

13. The ankle brace of claim 9 wherein said flexible lateral portion has an eyelet formed thereon rearwardly of said plurality of spaced-apart first eyelets thereof and wherein said flexible medial portion has an eyelet formed therein rearwardly of said plurality of spaced-apart first eyelets thereof; said second end of said flexible and stretchable lateral tensioning cord extending through said eyelet which is positioned rearwardly of said plurality of spaced-apart first eyelets of said flexible lateral portion for connection to said flexible lateral portion; said second end of said flexible and stretchable medial tensioning cord extending through said eyelet which is positioned rearwardly of said plurality of spaced-apart first eyelets of said flexible medial portion for connection to said flexible medial portion.

14. The ankle brace of claim 9 wherein a reinforcing member is positioned at the inner side of said flexible lateral portion and is secured thereto and wherein a reinforcing member is positioned at the inner side of said flexible medial portion and is secured thereto.

15. The ankle brace of claim 9 wherein a reinforcing member is positioned between said fourth non-stretchable strap and said third strap.

* * * * *